United States Patent [19]
Wolfbeis et al.

[11] Patent Number: 4,568,518
[45] Date of Patent: Feb. 4, 1986

[54] SENSOR ELEMENT FOR FLUORESCENCE-OPTICAL MEASUREMENT

[75] Inventors: Otto Wolfbeis; Herbert Kroneis; Helmut Offenbacher, all of Graz, Austria

[73] Assignee: AVL AG, Schaffhausen, Switzerland

[21] Appl. No.: 557,209

[22] Filed: Dec. 2, 1983

[30] Foreign Application Priority Data

Dec. 6, 1982 [AT] Austria ................. 4443/82

[51] Int. Cl.$^4$ ............... G01N 21/64; G01N 31/22
[52] U.S. Cl. .......................................... 422/56; 427/2;
427/157; 427/162; 428/290; 436/163; 436/172
[58] Field of Search ............... 422/56, 57; 436/172,
436/163, 169; 428/290; 427/2, 157, 162

[56] References Cited

U.S. PATENT DOCUMENTS

| | | | |
|---|---|---|---|
| 2,798,850 | 7/1977 | Voigtman et al. | 210/502.1 |
| 3,616,251 | 10/1971 | Lecco | 422/56 |
| 3,904,373 | 9/1975 | Harper | 436/169 |
| 4,003,707 | 1/1977 | Lubbers et al. | 436/172 |
| 4,029,597 | 6/1977 | Neisius et al. | 422/56 X |
| 4,200,110 | 4/1980 | Peterson et al. | 422/58 |
| 4,271,227 | 6/1981 | Muller et al. | 428/290 X |
| 4,287,153 | 9/1981 | Towsend | 422/56 |

Primary Examiner—Arnold Turk
Attorney, Agent, or Firm—Watson, Cole, Grindle & Watson

[57] ABSTRACT

Fluorescence-optical indicator material is chemically bonded in a network structure permeating a carrier membrane of the sensor element. As this network structure is independent of the membrane and not chemically bonded thereto, the properties of the membrane and the indicator are not affected by the immobilization.

4 Claims, No Drawings

SENSOR ELEMENT FOR FLUORESCENCE-OPTICAL MEASUREMENT

BACKGROUND OF THE INVENTION

The present invention relates to a sensor element for fluorescence-optical measurements, comprising a carrier membrane with fluorescent indicator material immobilized thereon.

DESCRIPTION OF THE PRIOR ART

For the measurement of pH values glass electrodes according to the potentiometer principle are widely used. For example, such sensors are used for pH-analysis of biological fluids, e.g., for blood gas analysis. The main disadvantage of this method is that the entire measurement system is essentially made up of two parts, i.e., a measurement electrode and a reference electrode. In particular, measurement problems arise because the necessary reference electrode is subject to failure.

For this reason it has been attempted to measure pH values by means of optical methods using so-called pH indicators. Such methods are based on the utilization of a pH dependent interaction of certain materials with light.

pH indicators usually are molecules which can absorb light of a certain wavelength, the degree of this absorption depending on the pH value.

pH measurements based on the above absorption principal may be performed in two ways:

(a) After adding pH indicators to the sample material, the light absorption of sample medium and indicator is measured with suitable equipment (cuvette, photometer). This method has the following disadvantages:
high indicator consumption
time consuming
optical influences exerted by the sample material.

(b) This alternative is described in German laid-open print No. 28 51 138, for instance, disclosing a fibre optical pH probe for implantation in tissues for physiological studies. This probe consists of an ion-permeable membrane in the shape of a hollow oblong cylinder, and of two optical fibers arranged parallel to each other. The hollow membrane, whose pores should be permeable to hydrogen ions, is filled with a dyeing medium of pH indicator properties.

One of the two optical fibres is connected to a light source on its one end, whereas the other fibre is connected to the light detector.

In this way the indicators are separated from the sample material such that two chambers are formed, one for the sample material and one for the indicator material. An exchange of protons between indicator and sample material chambers will permit the pH value of the sample material to be determined by measuring light absorption in the indicator chamber.

For pH indicators of the above properties fluorescent molecules may be used to advantage. In this case a certain percentage of the light absorbed is given off as fluorescent light by the indicator molecule. If the light absorption of a fluorescent molecule actually is pH dependent, this dependency is transmitted to the intensity of the fluorescent light. Thus, pH values can be determined by measuring the intensity of the fluorescent light of fluorescent pH indicators. Such indicators are listed in "Practical Fluorescence" (Guildbault, 1973), for example, in the chapter on "Fluorescent Indicators".

Among the advantages resulting from the use of fluorescent indicators are
high sensitivity
spectral distinction between excitation and emission light
great variety of possible locations of light source and light receiver.

These benefits will allow test equipment to be configured such that planar layers of indicator material will interact with the sample material on one side, whereas the other side of such layers is provided with lighting and light measuring devices.

When manufacturing such planar layers of indicator material, it must be borne in mind that, although the indicator molecules should be permitted to interact with the protons of the solvent, they should not be washed out by the sample material. In addition, the planar layer of indicator material should be mechanically stable, and concentration of the indicator material should be sufficiently high.

pH indicators are immobilized in hydrophilic polymer membranes by covalent bonding of the indicator and the membrane material. For this purpose either the indicator, the polymer membrane, or both, must be provided in activated form.

Activation is usually achieved by introducing reactive groups, amino groups. In this way indicator substances such as $\beta$-methylumbelliferone or fluorescein derivatives were successfully bonded to cellulose.

This immobilization will cause the sensor element to lose mechanical resistance, however, and will make it brittle and unsuited for re-use. Besides, the covalent bond will lead to shifts in the fluorescence-optical properties, which in turn may entail falsified measurement results.

Indicators may also be immobilized by encapsulation in suitable materials, e.g., as described in German laid-open print No. 23 60 384. Such "nanocapsules" are filled with aqueous indicator solution; the wall of the capsule is permeable to protons, but impermeable to the indicator substance.

For the manufacture of pH sensors these capsules for their part will have to be immobilized in planar array.

Mechanical instability, low indicator loading densities and poor response times are but some of the drawbacks of these known and described types of sensors.

Another possibility of immobilizing pH indicators is by bonding the indicators to the surface of a transparent carrier which is inert and mechanically stable.

The obvious method presenting itself is immobilization of the pH indicator on a chemically reactive material whose mechanical properties are less suited, e.g., cellulose, which is then placed on a stable and transparent carrier, such as glass or polyacrylic ester.

This method of immobilizing fluorescent indicators on cellulose or glass is known. It uses cellulose or glass which has been furnished with a free amino group in one or several preceding steps of reaction. The reactive groups of an indicator, e.g., fluorescein isothiocyanate, will then react on this amino group.

All known methods of immobilization pertaining to glass surfaces suffer from the disadvantage that the surface will take up only a relatively small amount of bonded immobilized material in a single layer. If the indicator substance is being immobilized on a pulverized material, however, such as glass powder, whose specific surface area is much larger, no mechanical stability may be expected.

SUMMARY OF THE INVENTION

It is an object of the present invention to build a sensor membrane which is not brittle and which will provide an elastic and stable substrate for the indicator to be chosen in a sufficiently high concentration.

According to the present invention this is achieved by integrating into the carrier membrane an independent network structure containing the indicator material. Another feature of the invention is that the carrier membrane is made of cellulose and that the network structure permeating the carrier membrane comprises indicator material and material containing amino groups. The indicator material thus is an integrated part of the network structure permeating the carrier membrane.

According to a further embodiment of the present invention, a suitable method of manufacturing such a sensor element includes soaking a carrier membrane in a solution of some cross-linking material such that the membrane is permeated by this material, and of establishing a covalent bond between the cross-linking molecules permeating the carrier membrane and the fluorescent indicator molecules, thereby building a network containing the indicator and permeating the carrier membrane.

In a further embodiment the method of manufacturing a sensor element according to the present invention provides that washing and/or drying cycles be included between the individual steps of procedure, and that a solution of hexamethylene diamine be used as a cross-linking material; it is also proposed that a solution of polyethyleneimine be used as a cross-linking material.

In another embodiment of the present invention the indicators used for cross-linking the network material permeating the carrier membrane carry at least two reactive groups (in the sense of a cross-linking reaction), preferably sulphonyl chloride groups.

Furthermore, the sensor element may be utilized for fluorescence-optical measurement of pH values and for blood gas analysis.

The invention will now be further explained by way of a practical example.

PREPARATION OF A NETWORK IN CELLULOSE

Dip a membrane of 10 $\mu$m thickness ("Cuprophan" dialyzing membrane, Enka-Membran, Wuppertal, 5×5 cm) into a solution of hexamethylene diamine (8 grams per 10 ml water) or polyethyleneimine (40%), and soak for two days. After two days a sufficient number of diamine chains will have embedded themselves in the network structure of the cellulose membrane. Afterwards, rinse in water for one minute. Place the membrane on a glass tray and pour on approximately 2 ml of a solution of 4 mg 1-acetoxypyrene-3,6,8-trisulphochloride in dioxane.

Add 1 ml of a 5 percent solution of sodium hydrogen carbonate and gently move the membrane to and fro. Rinse with water and dip the membrane into a 20 percent solution of sodium carbonate for 5 minutes, in order to split off the protecting acetate group. Repeat treatment with dioxane and sodium hydrogen carbonate solutions. The membrane will exhibit blue fluorescence first; after treatment with sodium carbonate solution fluorescence will turn to a vivid green. Soak the membrane in distilled water for one or two days; renew water several times.

In this way an independent network will build up within the netted structure of the cellulose membrane, which will not enter into a chemical bond with the membrane and will therefore lead to no reaction causing brittleness of the sensor element. Although points of contact will develop due to interpenetration of the individual networks and the creation of loops, there will be no covalent bond or cross-linkage between the networks. However, a chemical bond will be formed between the indicator and its carrier network which, as already pointed out, is embedded within the network of the cellulose membrane without any covalent bond. Once the indicator has been bound to the membrane in such a way, it can no longer be washed out, although it should be noted once again that there is no covalent bond between indicator substance and cellulose. In this case immobilization has been achieved by means of an interpenetrating network.

We claim:

1. A flexible sensor element useful in making fluorescence-optical measurements, said sensor element comprising a carrier membrane and an immobilized network structure integrated within said carrier membrane, said immobilized network structure including a fluorescent indicator material, said fluorescent indicator material being non-chemically bonded to said carrier membrane.

2. A flexible sensor element as defined in claim 1, wherein said carrier membrane consists of cellulose.

3. A flexible sensor element as defined in claim 1, wherein said flexible sensor element consists of said carrier membrane and said immobilized network structure integrated within said carrier membrane.

4. A flexible sensor element useful in making fluorescence-optical measurements, said sensor element comprising a carrier membrane and an immobilized network structure extending within said carrier membrane, said immobilized network structure including a fluorescent indicator material, said fluorescent indicator material being non-chemically bonded to said carrier membrane, said flexible sensor element being made by the steps of
 (a) providing a carrier membrane,
 (b) soaking said carrier membrane in a solution of cross-linking material until said carrier membrane is permeated with said cross-linking material,
 (c) adding a fluorescent indicator material to said carrier membrane in step (b), and
 (d) allowing said network structure containing said fluorescent indicator material to form within said carrier membrane.

* * * * *